United States Patent
Herzog et al.

(10) Patent No.: US 10,647,663 B2
(45) Date of Patent: May 12, 2020

(54) HIGH PURITY HCN FROM ACRYLONITRILE CO-PRODUCTION

(71) Applicant: INVISTA NORTH AMERICA S.A.R.L., Wilmington, DE (US)

(72) Inventors: Benjamin D. Herzog, Wichita, KS (US); Milind V. Kantak, Wilmington, DE (US)

(73) Assignee: INVISTA North America S.a.r.l., Wilmington, DE (US)

( * ) Notice: Subject to any disclaimer, the term of this patent is extended or adjusted under 35 U.S.C. 154(b) by 186 days.

(21) Appl. No.: 15/745,166

(22) PCT Filed: Jul. 22, 2016

(86) PCT No.: PCT/US2016/043446
§ 371 (c)(1),
(2) Date: Jan. 16, 2018

(87) PCT Pub. No.: WO2017/015521
PCT Pub. Date: Jan. 26, 2017

(65) Prior Publication Data
US 2018/0208548 A1 Jul. 26, 2018

Related U.S. Application Data

(60) Provisional application No. 62/196,341, filed on Jul. 24, 2015, provisional application No. 62/195,436, filed on Jul. 22, 2015.

(51) Int. Cl.
| | | |
|---|---|---|
| C07C 253/34 | (2006.01) | |
| C01C 1/245 | (2006.01) | |
| C01C 1/28 | (2006.01) | |
| C01C 3/02 | (2006.01) | |

(52) U.S. Cl.
CPC ............ *C07C 253/34* (2013.01); *C01C 1/245* (2013.01); *C01C 1/28* (2013.01); *C01C 3/0212* (2013.01); *C01C 3/0229* (2013.01); *C01C 3/0295* (2013.01)

(58) Field of Classification Search
CPC ... C07C 253/34; C01C 3/0212; C01C 3/0229; C01C 3/0295; C01C 1/245; C01C 1/28
See application file for complete search history.

(56) References Cited

U.S. PATENT DOCUMENTS

| | | | | |
|---|---|---|---|---|
| 2,706,675 A | * | 4/1955 | Chatelain | .................. C01C 3/04 423/372 |
| 3,360,355 A | * | 12/1967 | Horsley | ............... A01C 23/024 71/61 |
| 4,234,510 A | | 11/1980 | Wu | |

(Continued)

FOREIGN PATENT DOCUMENTS

WO 2017/015521 A1 1/2017

OTHER PUBLICATIONS

Kirk Othmer, "Encyclopedia of Chemical Technology", Fourth Edition, vol. 7, pp. 753-782.

(Continued)

*Primary Examiner* — Anthony J Zimmer
(74) *Attorney, Agent, or Firm* — Invista North America S.A.R.L.

(57) ABSTRACT

Disclosed is a process for co-manufacture of ACRN and HCN with improved HCN selectivity and reduced solids formation in a shared product recovery section.

13 Claims, 1 Drawing Sheet

(56) References Cited

U.S. PATENT DOCUMENTS

| | | | | |
|---|---|---|---|---|
| 6,339,169 B1* | 1/2002 | Hunt | ............... | C07C 253/34 |
| | | | | 558/319 |
| 6,413,485 B2* | 7/2002 | Seely | ............... | C01C 3/0212 |
| | | | | 423/376 |
| 8,585,870 B2 | 11/2013 | Basham et al. | | |
| 2002/0143131 A1 | 10/2002 | Ward et al. | | |
| 2005/0187401 A1 | 8/2005 | Godbole et al. | | |

OTHER PUBLICATIONS

International Preliminary Report on Patentability and Written Opinion Received for PCT Patent Application No. PCT/US2016/043446, dated Feb. 1, 2018, 8 pages.

International Search Report and Written Opinion received for PCT Patent Application No. PCT/US2016/043446, dated Oct. 21, 2016, 9 pages.

J. M. Pirie, "The Manufacture of Hydrocyanic Acid by the Andrussow Process", Platinum Metals Rev., 1958, 2, (1), pp. 7-11.

* cited by examiner

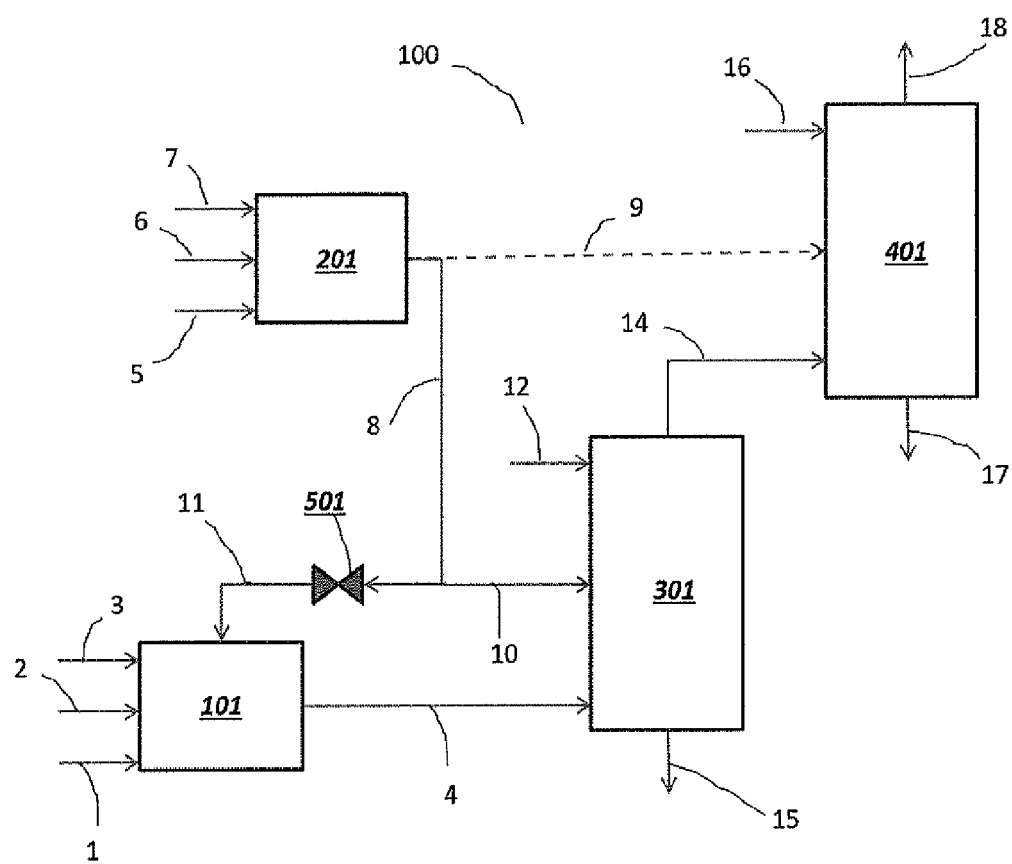

HIGH PURITY HCN FROM ACRYLONITRILE CO-PRODUCTION

FIELD

This present disclosure relates to a process for the co-manufacture of acrylonitrile and hydrogen cyanide.

BACKGROUND

Acrylonitrile (ACRN) is an important monomer for the synthesis of various polymers including acrylic fibers, synthetic rubbers, nylons, and is the starting material for acrylic acids and acrylamide. Processes to prepare ACRN include the Sohio Process in which propylene reacts with ammonia and oxygen (air) over a catalyst at elevated temperatures ("ammoxidation"). Hydrogen cyanide (HCN) and acetonitrile (AN) are produced as by-products.

HCN is a valuable by-product and is used, for example, as a starting material for the synthesis of various polymers, including polyamides, and chemicals.

Methanol injection to the ACRN reactor can increase HCN production in the Sohio Process, decreasing the ACRN:HCN weight ratio in the raw effluent from 10:1 to 8:1.

U.S. Pat. No. 8,585,870 discloses a method for co-manufacturing HCN and ACRN from separate reactor systems with a combined recovery/purification system. The disclosed process charges the HCN reactor effluent to an absorber column and the ACRN reactor effluent to a quench column. The process then shares a combined recovery/purification system. Under some conditions, the combined recovery/purification process can form insoluble solids that can accumulate and plug equipment. The problem can be more noticeable at lower ACRN:HCN weight ratios (higher levels of HCN co-production).

SUMMARY

As a result of studying methods for integrating ACRN and HCN manufacturing processes, we have found that under some conditions, the combined recovery/purification process can form insoluble solids that can accumulate and plug equipment. The problem can be more noticeable at lower ACRN:HCN weight ratios (higher levels of HCN co-production).

Disclosed is a process for co-manufacture of ACRN and HCN comprising:

(a) operating an ACRN process and a HCN process in parallel with separate reactor systems to co-produce an ACRN reactor product stream and a HCN reactor product stream containing the co-produced HCN, respectively, wherein the HCN is produced from reaction of methane, ammonia, and oxygen (oxygen, enriched air, or air) or from methane and ammonia;

(b) quenching the ACRN reactor product stream and the HCN reactor product stream in a common quench column with a first acid stream at pH of 7.0 or less to produce a quenched combined reactor product stream and recovering a first water purge from the quench column;

(c) in a single recovery/purification system, feeding the quenched combined reactor product stream comprising the quenched HCN reactor product stream and the quenched ACRN reactor product stream to an absorber column with water, to produce a combined product stream, having a weight ratio of ACRN to HCN of about 12 to 1 or less;

(d) treating the combined product stream sequentially in a recovery column, a decanter having an aqueous layer and an organic layer, and a heads column, wherein pH is controlled by addition of a second acid at pH of 7.0 or less in the absorber column and the recovery column, and at pH less than 4.5 in the decanter and heads column; and (e) separately treating the first water purge to recover ammonium salts and/or ammonia.

The first and second acids can be the same or different. The first acid is a mineral acid, and second acid can be a mineral acid or an organic acid. The mineral acid can include one or more of sulfuric, phosphoric and hydrochloric acids. For example, the first acid and/or the second acid can comprise phosphoric acid. It is desirable that the acid used has a strong chemical affinity for ammonia via salt formation.

The process may optionally include charging the HCN reactor product stream to the quench column and recovering unreacted ammonia as ammonium salt from the quench column bottoms. The process may optionally include operating the HCN process at as great as 80% ammonia conversion. HCN can be charged from the HCN process to the quench column upstream of the absorber column. Phosphoric acid can be used at pH of less than 7.0 for acid charge to the quench column for recovering ammonium salts. Non-limiting examples of ammonium salts may include diammonium phosphate, ammonium phosphate, ammonium phosphite, diammonium hydrogen phosphite, ammonium sulfate, etc. The ammonium salt formed depends on the acid used. The weight ratio of ACRN to HCN in the combined product stream is ≥2 to 1 and ≤12 to 1.

BRIEF DESCRIPTION OF THE DRAWING

The FIGURE is a simplified schematic representation of an embodiment of the present disclosure.

DETAILED DESCRIPTION

Provided herein is a process for co-manufacture of HCN and ACRN from separate reactor systems, and after combining the streams, refining them in a single recovery/purification system. The process comprises combining a stream comprising HCN, such as a HCN reactor product stream, with an ACRN reactor product stream, to produce a combined product stream, wherein the weight ratio of ACRN to HCN in the combined product stream is ≥2:1 and ≤12:1, for example, ≥2:1 and ≤10:1, to recover and purify ACRN and HCN with improved upstream time.

ACRN Reactor Product Stream

ACRN and HCN are co-produced in the disclosed process. ACRN can be produced via any suitable process that employs propylene or propane, ammonia and oxygen (air) over a catalyst at elevated temperatures, for example, the Sohio process in which HCN and AN are produced as co-products. Any source of oxygen can be used. For example, the oxygen source can be air. Useful catalysts are known and are generally based on bismuth-molybdates.

The reaction is carried out a temperature of ≥260° C. and ≤600° C., for example, ≥310° C. to ≤510° C., for example, ≥400° C. to ≤510° C. The pressure is typically 5 to 30 psig (34 to 207 kPa). The contact time is generally in the range of 0.1 to 50 seconds.

The ACRN product stream (reactor effluent) is a gas stream comprising unreacted reactants, ACRN, HCN, AN and water. The ACRN product stream passes through a quench column into which acidified water (at pH of 7 or less) is fed to lower the temperature of this stream and to remove any unreacted ammonia. If phosphoric acid is used as the quench acid, the unreacted ammonia can be recovered and recycled back into the process as a reactant. Alternatively, sulfuric acid may be added with the water to produce ammonium sulfate, which is removed as an aqueous stream. The ammonium sulfate can be sold as fertilizer as an aqueous solution or processed further into a solid that can be sold as fertilizer.

Stream Containing the Co-Produced HCN

The stream containing the co-produced HCN can be obtained from any source of HCN. Conveniently, HCN stream is provided as HCN product stream from a HCN synthesis reactor, for example, an Andrussow Process reactor as described by Pirie in *Platinum Metals Rev.*, 1958, 2, (1).

HCN can be produced from the reaction of natural gas (methane), ammonia, and oxygen over platinum, platinum-rhodium, or a platinum-iridium alloy catalyst in gauze form at or above atmospheric pressures and at temperatures greater than 1000° C. in the Andrussow Process. Alternatively, HCN can be produced from methane and ammonia passed through porous ceramic tubes lined or coated with platinum, at about 1300° C. in the Degussa BMA Process. Detailed descriptions of these processes are provided, for example, in the Encyclopedia of Chemical Technology (Fourth Edition, Volume 7, pp 753 to 782) edited by Kirk-Othmer. It is understood that alternate methods of HCN production exist, and the present disclosure is not limited to those referred to hereinabove.

The stream containing the co-produced HCN may also contain unconverted reactants, such as but not limited to methane, ammonia, nitrogen, and additional impurities, such as but not limited to hydrogen.

Combined Product Stream

The disclosed process integrates the production purification sections for a co-processed crude ACRN product stream and a co-processed crude HCN product stream to provide purified ACRN and HCN streams. The concentration of each component in the combined product stream can be varied to produce a weight ratio of ACRN to HCN ranging from ≤12 to ≥1, which is the typical weight ratio of ACRN to HCN produced in a standard Sohio ACRN process, to as low as 2 to 1. When the HCN production is increased, for example at ACRN:HCN weight ratios as low as 2:1, for example, between ≥2:1 and ≤5:1, the on-stream time of the co-processing equipment can be reduced due to accumulation of solids, for example, finely divided solids.

The ACRN:HCN weight ratio can be adjusted by increasing or decreasing the rate of HCN being fed, such as increasing or decreasing rate of production from the HCN synthesis reactor. The combined product stream is introduced into a recovery and purification system.

The co-produced ACRN and HCN product streams are combined in a quench column of a recovery/purification operation. The streams are then combined with water in the absorber column to provide an aqueous stream comprising HCN and ACRN, having a weight ratio of ACRN to HCN of about 12 to 1 or less.

Recovery and Purification

The disclosed process comprises passing the combined product stream into a quench column, an absorber column, followed by passing the absorption column bottoms effluent containing the nitriles products through a nitriles recovery and purification section. A typical nitriles recovery and purification section comprises of a series of distillation columns, decanters, and purification columns, for example, a recovery column, a decanter and a heads column. As is known to those skilled in the art, "column" herein refers to a distillation column. In the heads column, the crude HCN is separated from the crude ACRN, and sent to an HCN distillation column for further purification and then sent for additional reaction and/or to storage. The crude ACRN is sent from the heads column to a drying column then to a product column for further purification and storage. A detailed description of a typical recovery and purification process is known to those skilled in the art and is disclosed in U.S. Pat. No. 4,234,510 and Encyclopedia of Chemical Technology (Fourth Edition, Volume 7, pp 753 to 782) edited by Kirk-Othmer.

As will be appreciated by those skilled in the art, appropriate materials of construction should be used in the recovery and purification equipment, such as stainless steel rather than carbon steel, to protect equipment against higher concentrations of HCN relative to those of conventional Sohio ACRN processes.

Flammable gases, such as methane and hydrogen, relative to a standard ACRN product stream are present in the quench column as part of the combined product stream. Hydrogen, methane, and nitrogen, as well as other non-absorbing gases, are separated from the combined product stream and removed as off-gas from the top of the absorber column for incineration, or further separation. In the present disclosure, the concentration of HCN present in the absorber column is increased, for example up to about 5% by weight, relative to a typical Sohio process where the concentration of HCN is 1% by weight at the same location. Moreover, the HCN concentration in the decanter can be as high as 45% by weight. Therefore, for safe operation, at high HCN concentrations, conditions must be maintained to prevent HCN polymerization and/or decomposition.

In the process of this disclosure to accommodate the higher concentrations of HCN, there is provided a control system to monitor pH and temperature along the recovery/purification system. Specifically, through a combination of temperature control and pH control, conditions are maintained to prevent HCN polymerization from occurring. More specifically, in circulating aqueous streams, as are present in the absorber column, recovery column, and decanter, these streams are maintained at a pH 7.0 or less. The aqueous feed to the absorber column generally has a pH of ≥5.5 to ≤7.0. The absorber column is preferably maintained at a pH of ≥5.0 to ≤6.5, which is then fed to the recovery column. The pH is monitored in the absorber column and acid is added if needed to lower pH, as described below.

Preferably the pH of the recovery column is near neutral pH, that is, a pH of ≥6.8 to ≤7, for example, pH 6.8 to control acrolein in the system. If needed, a base, such as soda ash is added to the recovery column to raise pH.

Temperatures are also adjusted based on pH, as HCN polymerization is affected by a combination of pH and temperature.

Similarly, in organic streams, such as in the decanter, heads column and HCN column from which is recovered crude HCN, pH is controlled at a pH≤4.5, preferably at a pH of ≥3.8 to ≤4.2. Temperature is similarly controlled in combination with pH. For example, the decanter preferably has a temperature of less than about 50° C. and a pH of ≥3.8 to ≤4.2.

The control system can be any standard control system such as a distributed control system or other feedback control system. Devices are installed in the recovery/purification system, particularly on the decanter as part of the control system, to monitor and control the temperature and pH. The devices may include thermocouples, pH meters, feedback controllers, and control devices to adjust temperature, e.g., by increasing or decreasing coolant to a column and to adjust pH, e.g., by adding, increasing or decreasing flow of an acid to one or more of the absorber column, recovery column, decanter, heads column and HCN column. Under conventional operation, HCN concentrations are relatively low and acid addition was performed only in the heads column and in HCN distillation column.

The acid can be any acid capable of reducing the pH to ≤4.5, preferably ≤3.8. Suitable acids include (but are not limited to) glycolic acid, acetic acid, phosphoric acid, succinic acid, lactic acid, formic acid, glyceric acid, citric acid, fumaric acid, citraconic acid, maleic acid, sulfamic acid, esters of these acids, and combinations of two or more thereof. For example, the acid can be acetic acid.

In addition to pH, temperature is controlled. The temperature of the decanter can suitably be ≤50° C., for example, ≥38° C. and ≤42° C. Process cooling is normally controlled by cooling water circulation including in the decanter. It is understood that others methods of cooling is acceptable provided it is compatible with the materials of construction and does not interfere with the recovery and purification.

The quantity of HCN can also be selectively produced based on market need and can be reduced or increased without affecting the quantity of ACRN produced by having to feed methanol to the ACRN production reactor or changing the ACRN catalyst or process conditions. Likewise the quantity of ACRN can be selectively produced based on market need and can be reduced or increased without affecting the quantity of HCN produced.

An additional advantage is the elimination of the need to convert methane to methanol then to HCN improving the overall carbon balance of raw materials to final product. Another advantage of this disclosure is the ability to process large concentrations of HCN in the recovery and purification process while still preventing polymerization of HCN. Since risk of HCN polymerization increases with increasing HCN concentration it is surprising that the relatively high concentrations of HCN in the process of the present disclosure can be achieved with only limited HCN polymerization, and maintaining safe operation.

Some approaches to prevent polymerization can add significant equipment and costs. Some can require reducing the operating pressure, which also can reduce total output. Using a process of this disclosure, downtime can be reduced and plant output can be consistent with a typical ACRN process with minimal incremental equipment costs.

Overview of the FIGURE

The FIGURE is a simplified schematic representation of an embodiment of a HCN process and an ACRN process with co-processed products as disclosed herein.

In Embodiment 100, a $C_3$ hydrocarbon stream 1, anhydrous ammonia stream 2 and an oxygen source stream 3 are fed to an ammoxidation reactor system 101, wherein a fluidized catalyst bed is effective in converting the $C_3$ hydrocarbon into an unsaturated nitrile in the presence of ammonia and oxygen. The unsaturated nitrile is ACRN when propylene is used as $C_3$ hydrocarbon in Stream 1. The ammoxidation reactor system 101 produces a hot, gaseous effluent stream 4 rich in ACRN and contains byproduct AN and HCN. Stream 4 also contains excess ammonia and other inert gases. The hot effluent gas stream 4 is fed to a quench system 301 wherein an acidic, quench liquid stream 12 comes in intimate contact with the upflowing hot gases. The gas-liquid contact time in the quench system 301 is maintained such that 1) the hot gases are sufficiently cooled and 2) the excess ammonia present in stream 4 is extracted out as an ammonium salt via the quench liquid effluent stream 15. The flow rate and acidity of the quench liquid stream 12 are sufficiently maintained to effectively remove all ammonia feeding to the quench system 301 by salt formation. The temperature and concentration of the stream 15 is such that the ammonium salt is in solubilized form. The quench liquid effluent stream 15 is further processed to concentrate the salt and recover the quench liquid for re-use or disposed appropriately (not shown).

The cooled, gaseous effluent stream 14 from the quench system 301 is substantially ammonia-free and contains the ammoxidation reaction products, namely ACRN, AN and HCN. Stream 14 is fed to an absorber system 401 wherein an absorbent liquid stream 16 is intimately contacted with the upflowing gases in a counter-current mode. The conditions in the absorber system 401 and the stream 16 flowrate are maintained such that the nitriles are absorbed in the absorbent liquid and concentrated at the absorber bottoms stream 17. The nitriles-containing absorber bottoms liquid stream 17 is processed in a downstream conventional distillation train (not shown) for the recovery of ACRN, AN and HCN. The acidity in the absorbent liquid stream 16 is maintained to minimize undesired HCN polymerization during the nitriles recovery process. The non-condensable and non-absorbable components present in stream 14 concentrate at the absorber top stream 18 which is vented for disposal.

In an embodiment of the present disclosure, a stand-alone HCN synthesis reactor system 201 co-exists with the ammoxidation reactor system 101. A $C_1$ hydrocarbon (methane) stream 5, anhydrous ammonia stream 6 and oxygen source stream 7 are fed to the HCN synthesis reactor system 201, wherein a fixed bed of catalyst is effective in converting the $C_1$ hydrocarbon into HCN in the presence of ammonia and oxygen, such as an Andrussow reactor. Suitable sources of oxygen include oxygen recovered from air, oxygen-enriched air and air. The HCN synthesis reactor system 201 may be operated at as great as 80% ammonia conversion. The HCN synthesis reactor system 201 produces a gaseous effluent stream 8 that is rich in HCN and contains excess ammonia along with other inerts.

The $C_1$ hydrocarbon stream 5 may be optionally be obtained from a methane production facility (not shown). Alternatively, the $C_1$ hydrocarbon stream 5 may be obtained from a shale gas production facility. The gas production may be originating from a bio-gas facility, bio-digester, municipal/landfill waste gas generator, chemical facility or any other known industrial methane-containing gas producer. The quality of $C_1$ hydrocarbon stream 5 may be such that the higher ($C_2$+) hydrocarbon impurities are ≤20 wt %, for example, 15 wt %, 10 wt %, 9 wt %, 8 wt %, 7 wt %, 6 wt %, 5 wt %, 4 wt %, 3 wt %, 2 wt %, 1 wt %, 0.5 wt %, 0.1 wt %, 0.05 wt %, relative to the total gas composition.

One embodiment of the present disclosure allows for feeding less pure $C_1$ hydrocarbon stream 5 to the HCN synthesis reactor system 201. In another embodiment, the higher hydrocarbon impurities present in the $C_1$ hydrocarbon stream 5 may be converted to their respective nitriles in the HCN synthesis reactor system 201 which may be processed and recovered according to the present disclosure.

The HCN effluent stream 8 is routed to the quench system 301 present in the previously described ACRN process. Either a partial or complete portion of the stream 8 is fed to the quench system 301 via HCN gas stream 10. A flow control valve device 501 may be used to distribute the HCN effluent stream 8 between HCN gas stream 10 and stream 11. Stream 11 may be introduced into the ammoxidation reactor system 101 as a supplemental means for the ammoxidation catalyst fluidization. In that case the ammoxidation hot effluent gas stream 4 is the combined stream containing the ammoxidation reaction products and some or all HCN synthesis reaction products.

The excess ammonia present in the HCN gas stream 10 is removed in the quench system 301 due to the quench liquid stream 12 acidity. Any and all ammonia entering in the quench system 301 is thereby scrubbed out in the quench liquid effluent stream 15 as soluble ammonium salts. The cooled, gaseous effluent stream 14 rich in nitriles is processed further as described before. The present disclosure shows a practical and cost-effective way of increasing the production rate of high-purity HCN from a co-existing ACRN production facility.

In an embodiment where the HCN synthesis reactor effluent stream 9 (dotted line in the FIGURE) is directly fed to the absorber system 401 instead, i.e., by-passing the quench system 301, the excess ammonia present in stream 9 creates operational problems in the absorber system 401. Neither the acidity nor flowrate of the absorbent liquid stream 16 are sufficient to scrub and remove the entering ammonia as solubilized salts at the absorber bottoms stream 17. Salts tend to precipitate at the current absorber conditions and pose undesirable pressure increases and flow restrictions at the absorber bottom. Alternatively, the acidity and/or the flowrate of the absorbent liquid 16 may be increased but there are cost penalties and absorber bottlenecks to deal with which is impractical. Further, the ammonium salts, if present in the absorber bottoms stream 17, are required to be separated and removed before the nitriles downstream separation/recovery steps. Any ammonium salts that carry forward into the downstream nitriles recovery sections create lots of problems in terms of equipment scaling, plating and plugging of the reboiler tubes, undesirable side reactions, and therefore, must be avoided. For the disclosed process, feeding the HCN gaseous effluent stream 9 directly into the absorber system 401 is not a desirable integration for boosting the HCN production via integration with the ACRN plant.

The present disclosure is a practical and cost-effective way of increasing the production rate of high-purity HCN from a co-existing ACRN production facility.

EXAMPLES

The following Examples refer to a schematic flow diagram as illustrated in the FIGURE.

Example 1 (Schematically Illustrated Dotted Line 9 in the FIGURE)

In a commercial ACRN production facility, an ammoxidation reactor system 101 catalytically converts a $C_3$ hydrocarbon (stream 1), such as propylene, to ACRN in the presence of ammonia (stream 2) and oxygen source (stream 3). The fluidized-bed reactor produces a hot, gaseous effluent (stream 4) that is rich in ACRN with byproduct AN and HCN. The gaseous effluent is quenched in a counter-current quench column system 301 using a quench liquid (stream 12). The quench liquid is acidic (low-pH) such that the excess ammonia is efficiently scrubbed out of the reactor effluent. Organic or inorganic acids (such as sulfuric acid or phosphoric acid) are used for removing ammonia at the quench column bottom (stream 15) as soluble ammonium salts. The quenched product gases (stream 14) are then passed to a counter-current absorber column system 401 where absorbent liquid (stream 16) extracts the reactor products at the bottom (stream 17) while any non-condensable and non-absorbable components are vented as off-gas (stream 18). The crude product stream (17) is further processed in the downstream nitriles recovery and purification section (not shown) to produce high-purity ACRN by separating byproduct AN and HCN.

A crude HCN product stream 9 is produced in a stand-alone HCN synthesis reactor system 201 from a catalytic reaction between methane (stream 5), ammonia (stream 6) and oxygen source (stream 7). Stream 9 is fed to the absorber column system 401 along with the quench products (stream 14) from ACRN facility. Stream 14 is already depleted in ammonia through its quench treatment in 301 and therefore does not introduce ammonia in 401. The excess ammonia, present in the crude HCN product stream 9, reacts with the acidity in the absorbent liquid and produces an ammonium salt. The salt is observed to precipitate out at the absorber column bottom (stream 17), thereby, creating plugging and flow restriction as observed over time. The processibility of the absorber column 401 is affected due to the solids formation at the column base. It is now necessary to separate the crude nitriles products (ACRN, AN, HCN) from the precipitated solids via conventional techniques that add to processing cost and product yield loss. The product yields of HCN, ACRN and AN suffer due to the added complexity of dealing with the ammonium salts in stream 17. Also, the maintenance frequency for separation/recovery equipment over time, mainly distillation column bases and reboilers, is increased as a result of scaling and plugging by the solids at separation temperature and pressure conditions.

Example 2 (Schematically Illustrated Solid Lines 8 and 10 in the FIGURE)

The crude HCN product stream 9 of Example 1 is routed to the quench column 301 of Example 1 via Streams 8 and 10 along with the ammoxidation reactor gaseous stream 4. The quench liquid (stream 12) flowrate and acidity are adjusted for the combined ammonia entering in the quench column via streams 4 and 10. The quench column 301 is effective in scrubbing all excess ammonia from the entering feed. The scrubbed quenched gases (stream 14) are fed to the absorber column 401 of Example 1. The absorbent liquid flowrate (stream 16) is adjusted for the combined nitriles present in the quenched gas (stream 14). The absorber column 401 concentrates all nitrile products, i.e., ACRN, AN and HCN, at the bottom stream 17. There is no observed ammonium salt formation thereby no solid plugging in the absorber base.

The absorber bottom crude product stream 17 is processed in the downstream nitriles recovery and purification section (not shown) to product high-purity ACRN along with byproduct AN and HCN. High-purity HCN is produced at an increased throughput by integrating HCN and ACRN producing facilities with the already existing downstream equipment assets. The product ratio of ACRN:HCN after the purification step is 9:1 by weight.

Example 3

Sulfuric acid is added to the quench liquid stream 12 to lower its pH in the desired acidic range. For the Example 2 process, excess ammonia entering the quench system 301 via streams 4 and 10 is removed at the quench bottoms stream 15 as solubilized ammonium sulfate salt. The quench bottoms stream 15 containing the ammonium sulfate salt is concentrated using conventional techniques such as distillation, evaporation or crystallization or a combination thereof, the salt is isolated for commercial sale while the acid-depleted quench liquid is recycled back to the process after replenishing its acidity by sulfuric acid dosing.

The quench gaseous effluent stream 14 is depleted in ammonia and can be further processed in the absorber system 401 without observing salt formation or precipitation.

Example 4

Phosphoric acid is added to the quench liquid stream 12 to lower its pH in the desired acidic range. For the Example 2 process, excess ammonia entering the quench system 301 via streams 4 and 10 is removed at the quench bottoms stream 15 as solubilized diammonium phosphate salt. The quench bottoms stream 15 containing the diammonium phosphate salt is concentrated using conventional techniques such as distillation, evaporation or crystallization or a combination thereof, the salt is isolated for commercial sale while the acid-depleted quench liquid is recycled back to the process after replenishing its acidity by phosphoric acid dosing.

The quench gaseous effluent stream 14 is depleted in ammonia and can be further processed in the absorber system 401 without observing salt formation or precipitation.

Example 5

The HCN synthesis reactor system 201 is operated with high ammonia conversion to minimize the amount of unreacted ammonia in the crude HCN gaseous effluent stream (8 or 9). The HCN effluent stream may either be fed to the absorber column system 401 (dotted line 9), routed to the quench system 301 (solid lines 8 and 10) or some combination of the two. The quench liquid (stream 12) flowrate and acidity are adjusted to remove all excess ammonia fed to system 301. The absorbent liquid (stream 16) flowrate and acidity are adjusted to remove ammonia that enters to system 401 via stream 9. The liquid concentrations in 301 and 401 are maintained such that the ammonium salts remain in solution and do not precipitate out. The quench and absorber system operations are carried out without any flowline plugging due to precipitated salts. The reaction products effluent stream 17 is processed in downstream nitriles separation/recovery section (not shown) for purified HCN, ACRN and ACN.

Example 6

The crude HCN product stream 9 of Example 1 is partially routed to ammoxidation reactor system 101 of Example 1 via Streams 8 and 11 by opening the flow control valve device 501. A routed portion of the crude HCN product stream 11 supplements the ammoxidation catalyst fluidization. The ammoxidation reactor effluent (stream 4) along with the remaining portion of the crude HCN product (stream 10) are recombined in the quench system 301 for excess ammonia removal via stream 15. The use of routed stream 11, with components being indigenous to the ACRN production process, saves the inert gases required for catalyst fluidization in 101.

Depending on the required fluidization versus throughput load in 101, the flow control valve device 501 can be fully opened to route the entirety of crude HCN product stream 8 via stream 11 and by isolating the stream 10 feed to 301.

Example 7

The crude HCN reactor effluent stream 9 of Example 1 is passed through an ammonia scrubber (not shown) after the HCN synthesis reactor 201 to remove the excess, unreacted ammonia from stream 9. An appropriate concentration of inorganic acid (sulfuric or phosphoric acid) having a strong affinity for ammonia, such as sulfuric or phosphoric acid, is used in the scrubber wherein ammonia in the gaseous stream comes in intimate contact with the acidic scrubbing liquid in a counter-current manner. The gaseous ammonia reacts with the acid and the ammonium salt is formed in the downflowing liquid. The scrubber bottoms liquid effluent is obtained as an aqueous stream containing solubilized ammonium salts which can be further concentrated using conventional techniques such as distillation, evaporation or crystallization or a combination thereof for the recovery of ammonium salts for commercial sale while the acid-depleted quench liquid is recycled back to the process after replenishing its acidity by inorganic acid dosing.

The ammonia-scrubbed, crude HCN effluent stream 9 is fed to the absorber system 401 as in Example 1 for the recovery of nitriles via stream 17. There is no observed salt formation and precipitation at the absorber system 401 compared to Example 1.

Example 8

The ammonia scrubber of Example 7 is replaced with a solvent extraction unit (not shown). The crude HCN reactor effluent stream 9, as in Example 1, is passed through the solvent extraction unit wherein it comes in intimate contact with an organic solvent having a strong affinity for ammonia. The ammonia is absorbed out of the effluent gases and concentrated in the extracting solvent. The ammonia-laden solvent is further treated at pressure and temperature conditions to liberate the absorbed ammonia from the solvent, recovered as ammonia gas, dried and filtered for re-use in the ammonia feed system. The ammonia-depleted extraction solvent is further refined and re-used in the solvent extraction unit.

The ammonia-extracted, crude HCN effluent stream 9 is fed to the absorber system 401 as in Example 1 for the recovery of nitriles via stream 17. There is no observed salt formation and precipitation at the absorber system 401 compared to Example 1.

Example 9

The Example 2 process is repeated by feeding the combined effluents from individual reactor systems 101 and 201 to the quench system 301. The catalyst fines that are carried over from the individual reactor system in 101 are properly scrubbed out of the quench gaseous effluent stream 14 via the quench bottoms liquid stream 15. The catalytic activity of these fugitive fines is observed to be diminished as a result of quench system conditions. These inactive fines are filtered out of the stream 15 and appropriately disposed off. If a significant catalyst carryover is observed, the filtered solids accumulated over runtime are sent offsite for metals reclamation. Thus, the disclosed process integration is practically effective in handling catalyst fines generated in the reactors or otherwise. The product ratio of ACRN:HCN after the purification step is 9:1 by weight.

Example 10

The process of Example 1 is repeated, and the amount of HCN produced is varied to provide weight ratios of ACRN to HCN of 2:1, 3:1, 4:1, 5:1, 6:1, 7:1, 8:1, 9:1, 10:1, 11:1 and 12:1. In this Example, the pH is monitored and controlled at the absorber column, recovery column, decanter, heads column, and drying column by adding phosphoric acid to the column or decanter. At higher levels of HCN production, insoluble solids form and accumulate in the nitriles recovery and purification section, specifically, in the lower portions of columns, the decanter, and heat exchangers. The unit is shut down, accumulated solids are removed. The problem can be more noticeable at lower ACRN:HCN weight ratios (i.e., higher levels of HCN co-production).

Example 11

The process of Example 2 is repeated, and the amount of HCN produced is varied to provide weight ratios of ACRN to HCN of 2:1, 3:1, 4:1, 5:1, 6:1, 7:1, 8:1, 9:1, 10:1, 11:1 and 12:1 to show the ability to vary rate of co-manufacture of HCN and ACRN. In this Example, the pH is monitored and controlled at the absorber column, recovery column, decanter, heads column, and drying column by adding phosphoric acid to the column or decanter. At higher levels of HCN production, there is no observed ammonium salt formation thereby no solid plugging in the absorber base.

The absorber bottom crude product stream 17 is processed in the downstream nitriles recovery and purification section (not shown) to product high-purity ACRN along with byproduct AN and HCN. High-purity HCN is produced at an increased throughput by integrating HCN and ACRN producing facilities with the already existing downstream equipment assets.

The invention claimed is:

1. A process for co-manufacture of ACRN and HCN comprising:
   (a) operating an ACRN process and a HCN process in parallel in separate reactor systems to co-produce an ACRN reactor product stream and a HCN reactor product stream comprising HCN, respectively, wherein the HCN is produced from reaction of methane, ammonia, and oxygen or from methane and ammonia;
   (b) quenching the co-produced ACRN reactor product stream and the HCN reactor product stream in a quench column with a first acid stream at pH of 7.0 or less to produce a quenched combined reactor product stream and recovering a first water purge from the quench column;
   (c) in a single recovery/purification system, feeding the quenched combined reactor product stream comprising the quenched HCN reactor product stream and the quenched ACRN reactor product stream to an absorber column with water, to produce a combined product stream, wherein quenching the HCN reactor product stream along with the ACRN reactor product stream decreases the weight ratio of ACRN to HCN in the quenched combined reactor product stream so that the combined product stream from the absorber column has a weight ratio of ACRN to HCN of about 12 to 1 or less;
   (d) treating the combined product stream sequentially in a recovery column, a decanter having an aqueous layer and an organic layer, and a heads column, wherein pH is controlled by addition of a second acid at pH of 7.0 or less in the absorber column and the recovery column, and at pH less than 4.5 in the decanter and heads column; and
   (c) separately treating the first water purge to recover ammonium salt and/or ammonia.

2. The process of claim 1 wherein the first acid and the second acid independently comprise an organic or inorganic acid.

3. The process of claim 2 wherein the first acid and the second acid are independently sulfuric acid or phosphoric acid.

4. The process of claim 1 further comprising operating the HCN process at ≤80% ammonia conversion.

5. The process of claim 1 further comprising charging the HCN reactor product from the HCN process to an ammonia sorption column upstream of the absorber column.

6. The process of claim 5 further comprising flowing phosphoric acid at pH of ≤7.0 to the ammonia sorption column and recovering diammonium phosphate and/or ammonium phosphate.

7. The process of claim 5 further comprising flowing sulfuric acid at pH of ≤7.0 to the ammonia sorption column and recovering ammonium sulfate.

8. A process according to claim 1 wherein the weight ratio of ACRN to HCN in the combined product stream is ≥2 to 1 and ≤12 to 1.

9. A process according to claim 1 wherein the methane for producing the HCN of step (a) is supplied to the reaction in a methane charge stream containing ≥0.05 to ≤20 weight percent $C_2$ and heavier hydrocarbons.

10. The process of claim 9 wherein the methane charge stream contains ≥0.5 to ≤10 weight percent $C_2$ and heavier hydrocarbons.

11. The process of claim 10 wherein the methane charge stream contains ≥1 to ≤5 weight percent $C_2$ and heavier hydrocarbons.

12. The process of claim 10 wherein the methane charge stream contains ≥2 to ≤4 weight percent $C_2$ and heavier hydrocarbons.

13. The process of claim 1 wherein the weight ratio of ACRN to HCN in the combined product stream is ≥2 to 1 and ≤5 to 1.

* * * * *